(12) United States Patent
Marsh

(10) Patent No.: US 7,128,724 B2
(45) Date of Patent: Oct. 31, 2006

(54) CERVICAL SPINE BRACE AND TRACTION DEVICE

(75) Inventor: M. Lou Marsh, Del Mar, CA (US)

(73) Assignee: Ohana Medical Concepts, LLC, Del Mar, CA (US)

( * ) Notice: Subject to any disclaimer, the term of this patent is extended or adjusted under 35 U.S.C. 154(b) by 590 days.

(21) Appl. No.: 10/414,726

(22) Filed: Apr. 14, 2003

(65) Prior Publication Data

US 2004/0204666 A1    Oct. 14, 2004

(51) Int. Cl.
*A61F 5/08* (2006.01)

(52) U.S. Cl. .............................. 602/18; 602/17; 602/32

(58) Field of Classification Search .................. 602/18, 602/17, 32, 5, 19, 33–36; 606/61, 60, 241, 606/237; 128/DIG. 23
See application file for complete search history.

(56) References Cited

U.S. PATENT DOCUMENTS

| | | | | |
|---|---|---|---|---|
| 2,102,069 A | * | 12/1937 | Hanicke | 602/18 |
| 2,706,982 A | | 4/1955 | Hale et al. | |
| 2,791,999 A | | 5/1957 | Bustamante | 128/25 |
| 2,807,260 A | * | 9/1957 | Teufel | 602/17 |
| 2,820,455 A | * | 1/1958 | Hall | 602/18 |
| 2,885,234 A | * | 5/1959 | Larson | 403/46 |
| 3,177,869 A | * | 4/1965 | Bartels | 602/18 |
| 3,343,532 A | | 9/1967 | Zumaglini | 128/75 |
| 3,364,926 A | * | 1/1968 | Alderson | 602/18 |
| 3,765,412 A | | 10/1973 | Ommaya et al. | 128/132 |
| 3,776,224 A | * | 12/1973 | McFarland | 602/18 |
| 3,889,664 A | * | 6/1975 | Heuser et al. | 602/36 |
| 4,539,979 A | | 9/1985 | Bremer | 128/75 |
| 4,620,530 A | * | 11/1986 | Lanier et al. | 602/36 |
| 4,886,052 A | | 12/1989 | Calabrese | 128/75 |
| 4,913,135 A | * | 4/1990 | Mattingly | 602/18 |
| 5,005,563 A | * | 4/1991 | Veale | 602/18 |
| 5,046,490 A | * | 9/1991 | Young et al. | 602/17 |
| 5,109,835 A | | 5/1992 | McDonald et al. | 606/241 |
| 5,195,947 A | * | 3/1993 | Bode | 602/18 |
| 5,330,516 A | | 7/1994 | Nathan | 607/48 |
| 5,367,825 A | * | 11/1994 | Doring | 49/199 |
| 5,403,266 A | | 4/1995 | Bragg et al. | 602/5 |
| 5,507,718 A | | 4/1996 | Kabat | 602/18 |
| 5,651,764 A | * | 7/1997 | Chiu | 602/36 |
| 5,697,894 A | | 12/1997 | Gullichsen et al. | 602/32 |
| 5,728,054 A | | 3/1998 | Martin | 602/18 |
| 5,752,927 A | | 5/1998 | Rogachevsky | 602/18 |
| 5,823,982 A | | 10/1998 | Park | 602/36 |
| 5,950,628 A | | 9/1999 | Dunfee | 128/874 |
| 6,036,664 A | | 3/2000 | Martin, Sr. et al. | 602/5 |

(Continued)

*Primary Examiner*—Henry Bennett
*Assistant Examiner*—Huong Q. Pham
(74) *Attorney, Agent, or Firm*—Fitch, Even, Tabin & Flannery

(57) ABSTRACT

A cervical spine brace and traction device incorporates a forwardly open head and jaw brace which is adjustably supported vertically above a forwardly collar member. The brace and the collar member have cooperating lateral wall sections having mating arcuate surfaces that are juxtaposed and which include interengaging means that assure they remain precisely angularly aligned with each other while the vertical spacing between them is being changed. Support of the brace and adjustment is by pairs of laterally extending brackets which interconnect with rotatable rod mechanisms that carry coaxial right-handed and left-handed lead screw surfaces. A miter gear affixed to each rod in a central location mates with a cooperative miter gear affixed to a horizontal shaft that carries a starwheel at one end which permits smooth and accurate patient adjustment.

20 Claims, 2 Drawing Sheets

U.S. PATENT DOCUMENTS 6,045,522 A    4/2000    Grober ........................ 602/18
6,050,965 A    4/2000    Pillai ........................... 602/18
6,368,295 B1   4/2002    Lerman ....................... 602/17

* cited by examiner

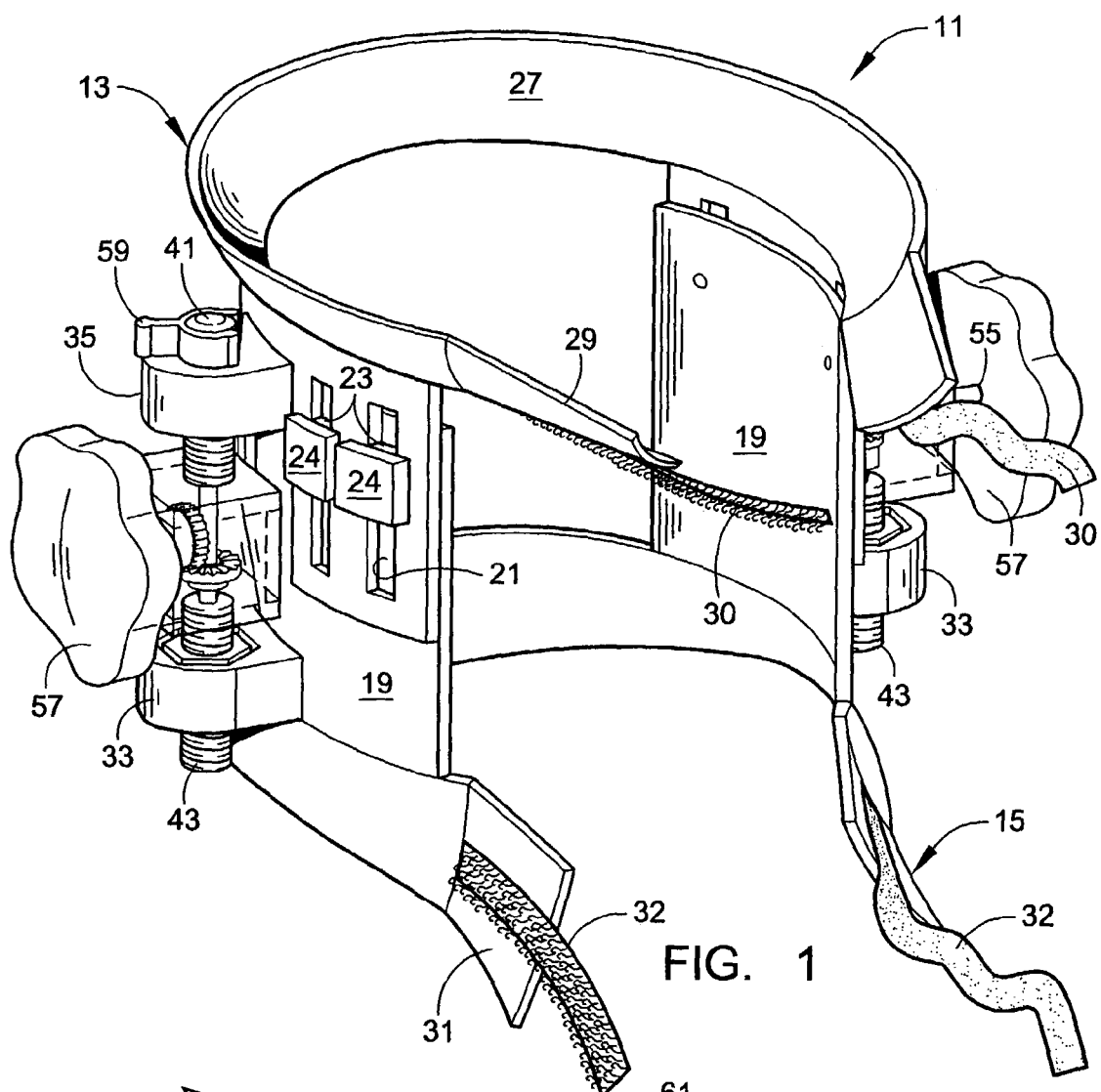
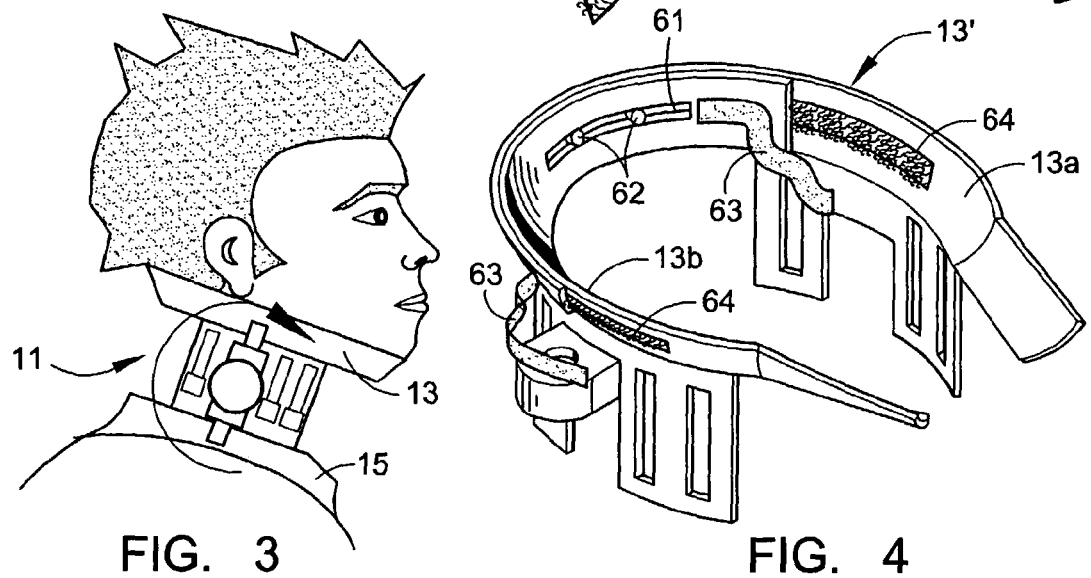
FIG. 1
FIG. 3
FIG. 4

CERVICAL SPINE BRACE AND TRACTION DEVICE

The invention relates to a mobile cervical spine brace and traction device that can be worn by a patient while carrying out normal daily duties, and more particularly to a device of this type that is lightweight, user-friendly and opens forwardly and is wide open in the rear to allow certain therapeutic treatment while it is being worn.

FIELD OF THE INVENTION

By age 55, about 95% of the population will experience some degenerative condition of the cervical spine that may cause neck pain and/or upper extremity pain and as much as one-third of that group may experience weakness. These non-tumorous and non-infectious conditions may include degenerative intervertebral discs, disc herniations, internal disc disruption, vertebral osteophytes or spur formation and spondylolisthesis, and they may potentially result in loss of disc space, height, encroachment on spinal nerve roots where they exit the spinal cord (radiculopathy), regional spinal cord compression (myelopathy) or vertebral joint instability. Moreover, yearly work-injury-related neck and/or back pain may frequently affect as much as 15 to 20% of the workforce; for example, the 1990 annual cost of neck and lower back care in the United States reached a staggering $85 billion.

Management of cervical pain, radiculopathy and myelopathy is either surgical or conservative, which may include anti-inflammatory medications, physical therapy, immobilization and traction. Surgical patients are always at risk for surgical complications including resultant quadriplegia and even death. Many recent publications by surgical and conservative therapists have, both retrospectively and prospectively, compared short and long term outcomes between the two treatment groups, and the consensus appears to be that, in the majority of patients, the outcomes are not truly distinguishable at one year.

Any intervention that would hasten the conservative recovery process, such as by facilitating independent patient participation in his/her own care, should also result in significant healthcare cost savings.

DESCRIPTION OF THE PRIOR ART

Cervical traction is the technique of removing the weight of the head from the cervical spinal axis and stretching the cervical column in order to relieve stress within the neck. This method can temporarily remove much of the pain experienced by people with cervical disorders. However, there is a downside to current traction methods, for most of the currently available traction devices are very cumbersome and difficult to use. Also, many must be used with direct interaction with a physician or other healthcare provider and, therefore, deny the patient mobility when in traction. Because these problems often affect the everyday lives of these patients, a portable traction device that can be used while the person goes about his daily tasks can prove to be a far better solution.

Previous mechanical efforts to support the cervical spine or apply traction thereto have generally fallen into certain distinct design trends. Full, solid cervical collars incorporating single or multiple, stacked pneumatic/air bladders are shown in the following United States patents: Pillai, U.S. Pat. No. 6,050,965; Rogachevsky, U.S. Pat. No. 5,752,927; Bragg, U.S. Pat. No. 5,403,266; Ommaya, U.S. Pat. No. 3,765,412; and Zumaglini, U.S. Pat. No. 3,343,532. Full, solid cervical collars incorporating multiple, stacked, fluid-filled bladders are shown in Park, U.S. Pat. No. 5,823,982. A full, but open, cervical collar, attached to a heavy chest/back apron/harness by adjustable spring-loaded rods is shown in Grober, U.S. Pat. No. 6,045,522, whereas McFarland, U.S. Pat. No. 3,776,224 shows a similar spring-tensioned device. Hanicke, U.S. Pat. No. 2,102,069 shows spaced pads carried by independent side braces that are angularly adjustable and are also longitudinal adjustable via sliding members and clamping screws. Threaded rod adjusters are shown in Hale, U.S. Pat. No. 2,736,314, in Hall, U.S. Pat. No. 2,820,455, and in Bartels, U.S. Pat. No. 3,177,869. Young, U.S. Pat. No. 5,046,490 places a peg in a hole on a sliding bar to fix the length and employs a hinge mechanism to control abduction and abduction in one embodiment and, in another, uses nuts on a threaded rod to cause a collar to slide up and down. A rack and pinion system is shown in Bustamante, U.S. Pat. No. 2,791,999. A halo to skull fixation device is attached to shoulder harness by calibrated threaded rods in Bode, U.S. Pat. No. 5,195,947 and in Gullichsen, U.S. Pat. No. 5,697,894. A full collar with a tracheal core aperture designed for static support and emergency immobilization is shown in Calabrese, U.S. Pat. No. 4,886,052, and a full collar with a ratchet and pawl mechanism for improved fit, emergency immobilization is shown in Martin, U.S. Pat. No. 6,036,664. U.S. Pat. No. 5,651,754 to Chiu shows a portable device for reforming the spine which utilizes a belt that is tightened about the waist and a motor-driven vertical rod that spaces a brace that engages the arm pits or the chin.

In spite of their claims to the contrary, none of the above-referenced prior art devices provides the patient with a truly user-friendly, simple, lightweight, easily installed and easily adjusted device which allows the application of appropriate, effective and efficient cervical traction by the patient in any setting, e.g. while the patient is an upright, mobile position. As a result, the search has continued to construct a device having these attributes.

SUMMARY OF THE INVENTION

The present invention provides a device which is capable of providing both cervical spine support as a brace and adjustable symmetric and asymmetric cervical spine traction in an entirely portable fashion. It weighs little more than a half of a pound and has controls that are easily managed even by arthritic fingers.

The invention provides a cervical spine brace and traction device which is forwardly open and wide open at the rear of the neck, and it thereby facilitates the use of concurrent therapy, such as application of heat or cold, specific neuromuscular electrical stimulation, such as T.E.N.S., care of tracheotomy stoma, and possible care of wounds. A forwardly open collar member has a pair of lateral regions designed to rest upon the clavicles or shoulder girdle of a user adjacent to the neck, with each lateral region including a superiorly extending wall section having a laterally extending bracket. Upwardly extending rod mechanisms are supported by these brackets, and each rod has co-axial, right-handed and left-handed lead screw surfaces. The upper ends of the rod mechanisms support a forwardly open, head and jaw brace, which has a head-support portion contoured to fit against the occipital region of the head and support means for a pair of lateral brackets that are threadably engaged with the upper ends of the rods. Interengaging means on the lateral wall sections of the collar member and juxtaposed lateral depending sections of the brace maintain both in longitudinal alignment while allowing them to be adjustably spaced vertically from each other. Adjustment means connected to each rod mechanism allows the user to easily and smoothly make fine adjustments to the spacing by simultaneously rotating each threaded rod mechanism the same amount to effect symmetric changes in traction or by rotating one side to a greater extent to adjust one side more or less than the other to effect asymmetric traction.

BRIEF DESCRIPTION OF THE DRAWINGS

FIG. 1 is a perspective view of a traction device embodying various features of the invention.

FIG. 2 is an exploded perspective view of the transaction device of FIG. 1.

FIG. 3 is side view of the traction device of FIG. 1 reduced in size and shown installed on a patient.

FIGS. 4 and 5 are fragmentary perspective views of alternative embodiments of traction devices embodying features of the invention.

DETAILED DESCRIPTION OF THE PREFERRED EMBODIMENTS

Figures 2, 5:
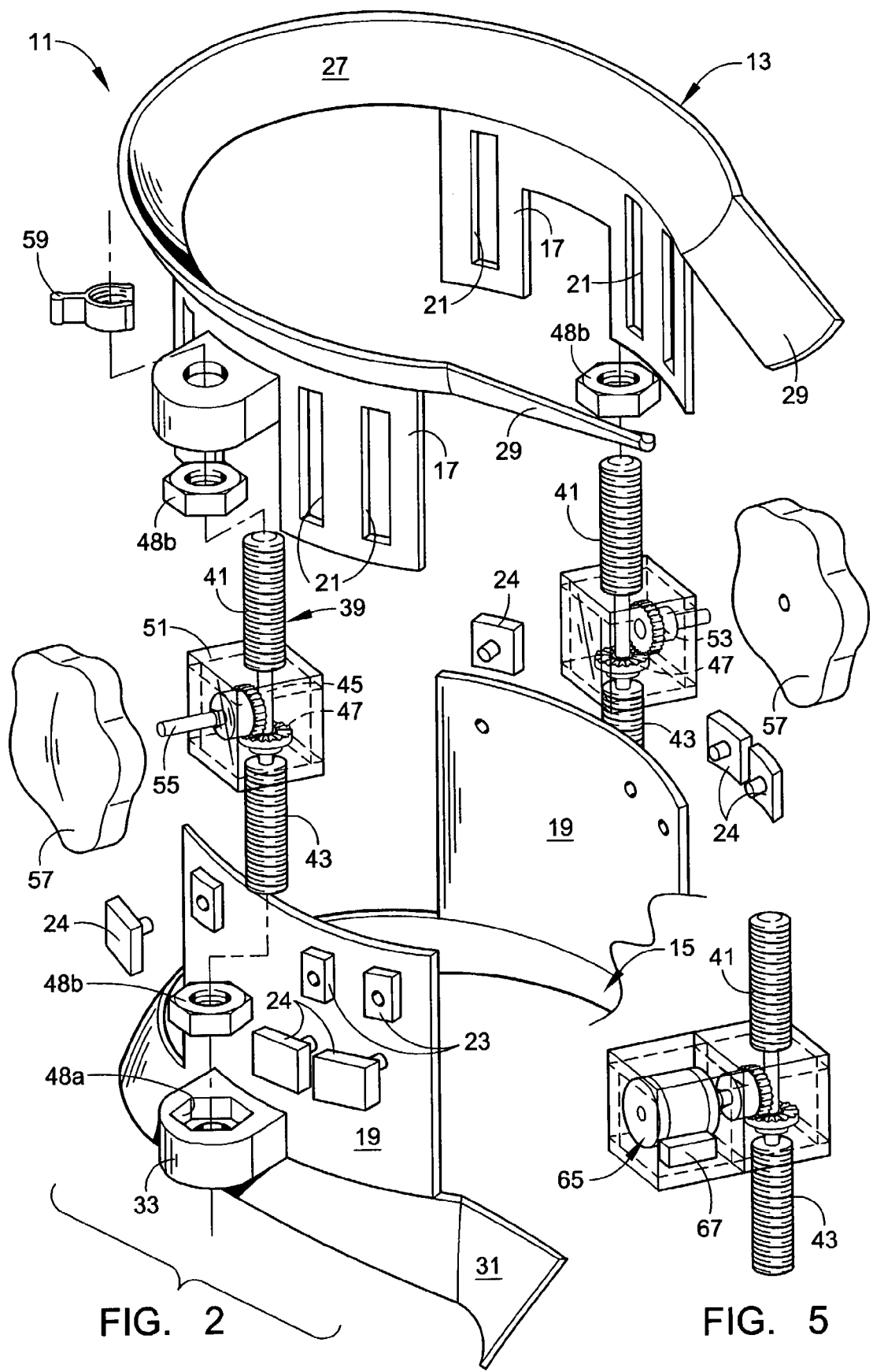

A traction device should be easy to put on and operate because the people in need of cervical traction often have limited dexterity due to their condition; for example, pinched nerves in the neck can cause loss of feeling and strength in fingers and hands. Furthermore, the device should be light enough so that a user does not mind carrying it when not in use, and it should provide comfortable wearing while performing tasks, e.g. work, when traction is being applied. Another desirable requirement is that the device should be of open design to allow for areas anterior and posterior where a hot/cold pack could be inserted or other treatments mentioned before may be effected.

Very generally, the traction device contains an upper brace that supports the occipital region of the head in connection with the mandibulae, i.e., lower jaws, and a lower collar that uses the clavicles or shoulder girdle for support. Along each side of the device are gearboxes that translate torque from a knob to a rotatable rod mechanism having two lead screw surfaces of opposite threading which allow for smooth positive movement at the upper and lower ends of each rotatable rod, as a result of one direction of rotational motion by the wearer, and consequent movement of the upper brace and lower collar either closer together or further apart. The gearbox assemblies are placed symmetrically about the head, and to obtain the proper symmetric traction desired, the user rotates both knobs to attain the specific spacing height for that user.

More specifically, a traction device 11 is shown for providing cervical spinal bracing and/or traction by exerting stretching force between the shoulders and a head brace 13 that is in contact with the occipital region of the head and extends forwardly (anteriorly) to support the angle and body of the mandibulae on each lateral side of the head. As best seen in the exploded perspective of FIG. 2, both the head brace 13 and a collar member or brace 15, that fits around and rests upon the clavicles or the shoulder girdle at the base of the neck, are forwardly open while being a continuous closed curve in the rear; however, the brace 13 and the collar member 15 are relatively narrow in the rear so as to leave the rear region of the neck wide open. This not only permits easy installation by the patient or wearer, but it facilitates ancillary treatment to allow concurrent therapy, as by the application of heat or cold to relieve pain or treatment with specific neuromuscular electrical stimulation, for example. The head brace 13 has a pair of depending lateral wall sections 17 which are arranged, shaped and proportioned to lie in juxtaposed relationship with a pair of upstanding lateral wall sections 19 that extend superiorly from the collar member 15. Interengaging means carried by these juxtaposed lateral wall sections assure that the collar and the head brace are maintained in the precise alignment, i.e., angular orientation, one to the other, while they are being moved vertically either nearer together or further apart.

In the illustrated embodiment, the lateral wall sections 17, 19 have a shallow arcuate cross sectional shape with surfaces that have substantially the same radius of curvature so that the exterior surface of each lateral wall section 19 lies in contact with the interior surface of the depending lateral wall sections 17, as seen in FIG. 1. To facilitate this precise alignment while allowing such relative motion, the depending lateral wall sections 17 are preferably each provided with 3 parallel slots 21, two of which lie forward of the ear, with the third being positioned rear of the ear. The slots 21 are preferably uniform in width throughout their length, and they receive 3 parallel, rectangular guides 23 affixed to the exterior surface of each of the lateral wall sections 19 that extend superiorly from support region of the collar. These guides 23 are interengagingly slidably received in the parallel slots 21, and the straight sidewalls of the rectangular guides 23 lie closely adjacent the elongated walls of the slots and thus assure that not only smooth relative motion between the brace and the collar occurs in a precise direction, but that, during such movement, the alignment of the brace and collar remains angularly precise. Moreover, the spacing of the singular slots 21 at a rearward location adds substantially to the overall stability of the spatial alignment between the brace and the collar. Once assembly is completed, small keepers 24 are affixed to the outer surfaces of the guides 23 by pins or the like to secure the interengagement.

The brace 13 preferably has a continuous curved or arcuate rear portion 27 that is contoured to comfortably abut the occipital region of the skull (as seen in FIG. 3) and a pair of oppositely disposed forward sections 29 that are contoured and angled to comfortably engage the undersurface of each mandible. It is preferably molded from a lightweight polymeric material; however, other suitable durable materials may be used. Preferably, a pair of interengaging Velcro hook and loop fastening straps 30 are affixed to the exterior surfaces of these front sections 29 so as to provide additional stability when the user is mobile; alternatively a single strap could be used that would attach to a strip affixed to the surface of the brace.

The collar member 15 has a continuous curved undersurface, which is shaped and proportioned to lie comfortably on the shoulder girdle of the wearer at a location close to the base of the neck. It is constructed of material similar to that of the brace so as to preferably aesthetically resemble each other. Ends 31 of the open collar member 15 that terminate at the front opening are preferably similarly provided with interengaging Velcro straps 32 or an alternative fastening arrangement, if desired for additional security and stability. Both the upper surface of the brace 13 and the undersurface of the collar member are preferably provided with padding or cushioning material (not shown), e.g. resilient polyurethane foam.

Pairs of apertured brackets of generally similar construction extend laterally, respectively, from surfaces of superiorly extending walls of the collar member and the depending walls of the brace; they are used to achieve the adjustment of the vertical spacing between the collar member and the brace. More specifically, lower brackets 33 extend from the exterior surface of the upstanding wall sections 19, and upper brackets 35 extend laterally from the exterior surfaces of the depending wall sections 17 of the brace. A rotatable rod mechanism 39 is supported by and extends between the upper and lower brackets on each side of the device 11, and it is designed to very precisely and smoothly adjust the vertical distance between the brace and the collar so as to either apply greater traction or reduce the traction force. The rod mechanism 39 is designed so as to balance out any torque by creating driving engagements both at the location of the upper bracket 35 and at the location of lower bracket 33 on each side of the device, and in this way to positively avoid the likelihood of binding and to assure smooth movement.

In the preferred embodiment, the rod 39 is one which has an upper lead screw surface 41 of one orientation, e.g., a right-handed thread, and a lower lead screw surface 43 of the opposite orientation, e.g., a left-handed thread. These screw threads are preferably cut into the surface of a rod of a suitable diameter so that the rod is an integral piece; however, the rod could be built as a composite member so long as the resultant structure has coaxial lead screw surfaces. A central section 45 of the rod 39, preferably located exactly halfway from each end, is of a reduced diameter, and it may be machined to have a miter gear surface 47, or alternatively such a gear may be affixed to the reduced diameter rod section. The upper and lower threaded sections 41, 43, which are preferably located at opposite ends of the rod 39, are received in the apertures of the brackets 35, 33. These apertures may be machined so as to have mating threads which interengage with the lead screw surfaces 41, 43 on the upper and lower sections of the rods, or the brackets 33, 35 might be molded so as to have hexagonal recesses 48*a* in their facing surfaces into which metal nuts 48*b* having mating threads are press fit and/or adhesively secured. Alternatively the brackets might be bifurcated to provide horizontal slots into such nuts could be inserted and secured in alignment. Accordingly, when the rod 39 on the right-hand side of the wearer's head, for example, is caused to be rotated clockwise as viewed from above, both rod threaded sections 41, 43 may enter more deeply into the brackets 35, 33 and thus cause the brace 13 and the collar member 15 to smoothly move toward each other, slightly reducing the amount of traction.

To drive the rod mechanisms 39, a small gear box 51 is supported on each rod at the location of the central section 45 of reduced diameter. The gear box 51 has apertures in its upper and lower ends so that it is journalled on the rod itself, and it is preferably a rectangular parallelepiped for convenience of construction. It contains a miter gear 53 mounted on a horizontal shaft 55 that extends through the gear box wall which the miter gear meshes smoothly with the miter gear 47 affixed to the rod; thus, its rotation drives the rod 39 in either clockwise or counterclockwise rotation. The horizontal shaft 55 is journalled in the gear box wall, preferably by a suitable bearing (not shown), and it carries a knob in the preferable form of a starwheel 57 affixed to its outer end which the patient will use to turn the miter gears, rotate the rod 39 and thus move the collar member and the brace either smoothly toward each other or away from each other. The shape of the starwheel 57 affords easy turning, and the locations are such that a patient can conveniently manipulate both starwheels simultaneously using both hands and thus smoothly and symmetrically apply either more or less traction in a precise manner. The precise change that is possible in this manner provides a potential for objective calibration, i.e., the number of screw rotations needed to achieve one millimeter of distraction of intervertebral space. This use of the two lead screw surfaces of opposite threading and the miter gear arrangement allows for very gradual and precise changes in the spacing between the brace and the collar member, and thus allows "fine tuning" of the amount of traction being applied.

Because a physical therapist may wish to limit the amount of traction that any individual patient can apply at any one time during rehabilitation, a locking clamp, a locking washer or nut or other such stop 59 is preferably provided near the end of one of the lead screw surfaces of each rod 39. Illustrated is such a stop clamp 59 which is manufactured to have a interior surface that interengages with the threads 41 at the upper end of the rod. It might be molded from a rigid plastic or preferably made of metal; it is designed to snap around the threaded rod and remain tightly in one place. A short tang extends from a central location to allow its easy placement or removal. Thus, it allows the physical therapist to set a maximum distance to which the brace and the collar member can be spaced apart, so that, when such distance is reached, the lock clamp 59 will engage top surface of the upper bracket 35, for example, preventing any further rotation of the rod by the patient that would tend to drive the brackets 33 and 35 further apart. This lock 59 may, if desired, be constructed so that it can only be moved or removed via the use of a special tool, so that is must otherwise remain in the precise location where the physical therapist has set it. For example, the two open ends may be linked to each other by a clamping screw which has a head designed to require a special tool to allow it to be tightened and loosened.

The neck is one of the more vulnerable parts of the human body and is a frequent cause of human discomfort; however, often only a small amount of traction is necessary to provide very effective relief for neck problems and sometimes increasing relief will result from increasing traction. However, there will likely be a threshold point that will be reached beyond which additional traction may cause overwhelming nausea and pain. Fortunately, such symptoms can be easily avoided by the "fine tuning" that is made possible by the illustrated construction and the starwheel knob controls.

Traction will gradually increase the spacing between a patient's vertebrae, and damaged cartilage and tissue between the vertebrae then may often swell to fill this space. When this occurs, should traction subsequently be removed too quickly, the swollen tissue between the vertebrae will often be pinched and cause severe pain. Thus, to avoid this potential problem, one should remove traction at a slow and comfortable rate, and such is made possible by the unique design of coaxial lead screw surfaces that can be simultaneously and precisely rotated through miter gear drives conveniently accessible to the patient. This particular adjustment mechanism not only allows a patient to make a quick and easy reduction in the amount of traction to relieve nausea, should any unexpected difficulty be encountered when increasing traction, but also the beneficial combination of the miter gear arrangements with the pairs of coaxial lead screw surfaces facilitates, the release of traction at any time in a carefully controlled manner so the patient should be safe from tissue damage. Moreover, both symmetric and asymmetric traction are readily facilitated.

Although the invention has been illustrated with regard to a preferred embodiment, it should be understood that the scope of the invention is defined by the claims appended hereto and that changes and modifications as would be obvious to one having the ordinary skill in this art may be made without deviating therefrom and that such changes may enhance the overall performance of the traction device. For example, although the brace and collar member illustrated in FIG. 1 are both made of a unitary construction, each of them may be made in two pieces so as to be adjustable with each other; shown in FIG. 4 is such a brace 13' formed of two halves 13a and 13b. Suitable connecting means are included to adjustably join them in rigid interconnection and, in this manner, to allow the horizontal distance between the lateral sections of the brace 13' (and similarly of the collar member) to be adjusted in order to accommodate users having different sizes and/or configuration of heads and/or necks. The brace halves 13a and 13b are preferably formed to have the same radius of curvature so the surfaces will slide in a juxtaposed position as shown in FIG. 4. One of the halves, in the illustrated embodiment the inner half 13b, is provided with an elongated slot 61 that extends generally horizontally and accommodates a pair of smooth headed pins or rivets 62 that are fixed to the outer half 13a to provide this slidable, adjustable interconnection. Once the correct distance is set for a particular patient, Velcro fastening devices in the form of, for example, loose straps 63 at the end of each of the halves are fastened to cooperative strips 64 carried by the facing surface of the opposite half, both interior and exterior of the composite brace, which securely prevents the pair of interconnected halves 13a and 13b from opening up.

Sets of parallel elongated interengaging means in the form as generally shown, i.e. a pair of close together slots 21 forward and a single slot rearward of the adjusting rod 39, have been found to provide excellent stability while retaining the desired openness. The arrangement might be reversed, with the pair of slots placed rearward of the ear.

Because the device does not involve any shoulder girdle, chest harness or cranial fixation, the torso remains free, and this truly portable device, is not cumbersome and is, in every respect, user-friendly. The design of the device avoids any pressure on the mental process or chin, thus eliminating a potential physiologic reflex arc which might involve stimulation of the vagus nerve in the neck, which stimulation is often associated with unpleasant nausea and potentially dangerous heart rate reduction. Assuming the device is molded of plastic material, which is the preferred construction, e.g. by injection-molding, by vacuum-forming or by some similar process, suitable plastic materials which are radiolucent can be chosen so that the user may continue wearing the brace even when undergoing radiographic studies, and in some instances, such a construction might even enhance the use of x-rays.

In addition, if the patient might have only limited flexibility of arm motion, an adjustment unit can be provided which includes an electric motor device 65 as depicted in FIG. 5, such as that shown in U.S. Pat. No. 5,651,764, which would be useful for driving the miter gear 53 in either a clockwise or counterclockwise direction. Such an electric motor drive mechanism 65 could be operated by a hand-held or belt-supported finger-operated push-button controller (not shown) that might be connected through a wireless electronic connection to a control 67 mounted on the motor. A voice-activated controller could alternatively be incorporated as a part of the motor drive.

The disclosures of all of the U.S. patents set forth hereinbefore are expressly incorporated herein by reference. Particular features of the invention are emphasized in the claims which follow.

The invention claimed is:

1. A cervical spine brace and traction device comprising a forwardly open arcuate collar member having a pair of lateral regions designed to rest upon the shoulders of a user adjacent the neck, and a lateral wall section extending vertically from each of said regions, each of said lateral wall sections having a laterally extending bracket, an upwardly extending, rotatable rod mechanism supported by each of said brackets, said rod mechanisms each having a pair of coaxial right-handed and left-handed lead screw surfaces, a forwardly open, head and jaw brace including lateral wall sections having a pair of upper brackets through which said brace is supported on said rotatable rod mechanisms in overlying relationship with respect to said collar member, said brace having a head support region contoured to fit against the occipital region of the head, interengaging means on said lateral wall sections of said collar member and on said lateral wall sections of said brace for maintaining one in alignment with the other while allowing them to be adjustably moved relative to each other, and adjustment means connected to said rotatable rod mechanisms whereby traction may be applied to the cervical spine by causing said brace to be smoothly raised above said collar member or in a desired position.

2. The device according to claim 1 wherein said brace extends forwardly from said occipital support region to a pair of regions which support each mandible of a user at its normal angle.

3. The device according to claim 1 wherein each of said brackets includes a mating threaded portion threadably interconnected with one of said lead screw surfaces.

4. The device according to claim 3 wherein said adjustment means includes a unit in which a miter gear is rotatably mounted to engage a cooperative miter gear which is affixed as part of said rod mechanism.

5. The device according to claim 4 wherein each said adjustment means includes a finger-manipulable starwheel connected to a shaft for rotating said miter gear and wherein said unit is supported from said rod mechanism.

6. The device according to claim 4 wherein each said rod mechanism includes stop means associated with at least one lead screw surface for limiting the extent to which the spacing between said collar member and said brace can be extended.

7. The device according to claim 1 wherein said lateral wall sections of said brace include pairs of depending wall surfaces which each include a generally vertical slot.

8. The device according to claim 7 wherein said depending wall surfaces are arcuate and are located on opposite lateral sides of the device extending forward of the patient's ear.

9. The device according to claim 7 wherein said lateral wall section of said collar member include a lug which is slidably received in said vertical slot.

10. The device according to claim 2 wherein said lateral wall sections of said brace include a pair of parallel slots that extend generally vertically from said mandible support regions that are each contoured to engage a lower surface of the user's mandible, and wherein said lateral wall sections of said collar member each carry a pair of elongated lugs that are respectively slidably received in said pair of parallel slots.

11. The device according to claim 1 wherein said collar member and said brace are both made of two pieces, and wherein connecting means are provided for adjustably joining together each of said two-pieces in substantially rigid interconnection so as to allow the horizontal distance between said lateral regions of the device to be adjusted in order to accommodate users having different sizes and/or configurations of heads and necks.

12. The device according to claim 4 wherein an electric motor is provided for driving said miter gear in either clockwise or counterclockwise direction.

13. The device according to claim 12 wherein a voice-activated control is incorporated as a part of each said motor drive.

14. A cervical spine brace and traction device comprising
a forwardly open arcuate collar member having a pair of lateral regions designed to rest upon the shoulder region of a user adjacent the neck and a lateral wall section extending vertically from each of said lateral regions,
each of said lateral wall sections having a laterally extending bracket,
an upwardly extending, rotatable rod mechanism supported by each of said brackets, said rod mechanisms each including a rod having a coaxial right-handed and left-handed lead screw surfaces,
a forwardly open, head and jaw brace including a pair of upper brackets extending laterally from a pair of depending wall sections, through which brackets of said brace are supported on said of rotatable rod mechanisms,
said brace having a head support region contoured to fit against the occipital region of the head,
interengaging means on said lateral wall sections of said collar member and said brace for maintaining one in alignment with the other while allowing them to be adjustably moved relative to each other, and
adjustment means connected to central section of each of said rotatable rod mechanisms whereby traction may be applied to the cervical spine by rotating said rods as to effect simultaneous relative movement between said rods and said brackets causing said brace to be smoothly raised above said collar member.

15. The device according to claim 14 wherein each of said brackets includes a mating threaded portion threadably interconnected with one of said lead screw surfaces, and wherein a gear for rotating each of said rods is affixed thereto at a location between said lead screw surfaces.

16. The device according to claim 15 wherein said gear is a miter gear and wherein said adjustment means includes a unit in which a cooperative miter gear is rotatably mounted to engage said gear affixed as part of each of said rod mechanisms.

17. The device according to claim 16 wherein each said adjustment means includes a finger-manipulable starwheel connected to a shaft for rotating said miter gear and wherein said unit is supported from said rod mechanism.

18. A cervical spine brace and traction device comprising
an arcuate collar member formed with a pair of lateral regions designed to rest upon the shoulders of a user adjacent the neck and with a lateral wall section extending vertically from each of said lateral regions,
a laterally extending bracket affixed to each of said lateral wall sections,
two upwardly extending, rotatable rod mechanisms, each of which includes a rod having a pair of coaxial right-handed and left-handed lead screw surfaces and each of which is supported by one of said brackets via a mating threaded portion thereof,
ahead and jaw brace that includes (i) a head support region contoured to fit against the occipital region of the head and (ii) lateral wall sections,
interengaging means on said respective lateral wall sections of said collar member and of said brace for maintaining one in alignment with the other while allowing them to be adjusted relative to each other by relative vertical movement,
an upper bracket affixed to each of said lateral wall sections of said brace for supporting said brace on said two rotatable rod mechanisms via mating threaded portions of said upper brackets, and
adjustment means comprising a gear affixed to each of said rods at a location between said lead screw surfaces for rotating said rotatable rod mechanisms whereby traction may be applied to the cervical spine by causing said brace to be smoothly raised above said collar member in a desired position.

19. The device according to claim 18 wherein said gear is a miter gear and wherein said adjustment means includes a unit in which a cooperative miter gear is rotatably mounted to engage said miter gear.

20. The device according to claim 19 wherein said adjustment means includes one said unit mounted on each of said rotatable rod mechanisms, which unit includes a finger-manipulable starwheel connected to a shaft for rotating one of said miter gears.

* * * * *

UNITED STATES PATENT AND TRADEMARK OFFICE
CERTIFICATE OF CORRECTION

PATENT NO. : 7,128,724 B2
APPLICATION NO. : 10/414726
DATED : October 31, 2006
INVENTOR(S) : M. Lou Marsh It is certified that error appears in the above-identified patent and that said Letters Patent is hereby corrected as shown below:

Column 8, line 17, claim 1, after "member" delete "or"; Column 8, line 61, claim 9, delete "section" and insert --sections--; Column 9, line 7, claim 11, delete "two-pieces" and insert --two pieces--; Column 9, line 28, claim 14, after "having a" insert --pair of--; Column 9, line 33, claim 14, after "on said" delete "of"; Column 9, line 41, claim 14, after "to" insert --a--; Column 10, line 22, claim 18, delete "ahead" and insert --a head--.

Signed and Sealed this

Twelfth Day of June, 2007

JON W. DUDAS
*Director of the United States Patent and Trademark Office*